United States Patent
Maeda et al.

(10) Patent No.: US 11,376,287 B2
(45) Date of Patent: Jul. 5, 2022

(54) AGENT ACTING ON TRANSCELLULAR ION TRANSPORTER IN INTESTINAL TRACT, AGENT FOR ACTIVATING CHLORIDE CHANNEL, AGENT FOR PREVENTING OR TREATING RENAL DISEASE, OR AGENT FOR PROMOTING DEFECATION

(71) Applicant: Biofermin Pharmaceutical Co., Ltd., Kobe (JP)

(72) Inventors: Ayako Maeda, Kobe (JP); Masaki Shimakawa, Kobe (JP); Hiroshi Ohno, Kobe (JP)

(73) Assignee: Biofermin Pharmaceutical Co., Ltd., Kobe (JP)

( * ) Notice: Subject to any disclaimer, the term of this patent is extended or adjusted under 35 U.S.C. 154(b) by 273 days.

(21) Appl. No.: 16/343,696

(22) PCT Filed: Oct. 18, 2017

(86) PCT No.: PCT/JP2017/037698
§ 371 (c)(1),
(2) Date: Apr. 19, 2019

(87) PCT Pub. No.: WO2018/074514
PCT Pub. Date: Apr. 26, 2018

(65) Prior Publication Data
US 2019/0262408 A1  Aug. 29, 2019

(30) Foreign Application Priority Data
Oct. 20, 2016  (JP) .............................. JP2016-206422

(51) Int. Cl.
*A61K 35/745* (2015.01)
*A61P 1/10* (2006.01)
(Continued)

(52) U.S. Cl.
CPC .......... *A61K 35/745* (2013.01); *A61K 35/747* (2013.01); *A61P 1/10* (2018.01); *A61P 13/12* (2018.01); *C12N 1/20* (2013.01)

(58) Field of Classification Search
CPC ................ A61K 35/745; A61K 35/747; A61K 2300/00; A61K 35/74; A61K 35/741; A61K 35/742; A61K 35/744; A61K 31/7016; A61K 9/0053; A61K 9/0031; A61K 2035/115; A61K 31/7004; A61K 31/715; A61K 35/39; A61K 38/46; A61K 9/19; A61K 45/06; A61K 31/702; A61K 38/18; A61K 38/19; A61K 39/39; A61K 2039/505; A61K 2039/541; A61K 2039/544; A61K 2039/55; A61K 2039/55583; A61K 2039/577; A61K 2039/58; A61K 2039/70; A61K 39/0008; A61K 39/35; A61K 39/395; A61K 9/0034; A61K 9/0043; A61K 9/007; A61K 31/733; A61K 35/76; A61K 39/3955; A61K 8/60; A61K 8/731; A61K 38/00; A61K 8/022; A61K 9/4816; A61K 2035/11; A61K 2069/507; A61K 2039/521; A61K 2039/522; A61K 2039/55594; A61K 2039/585; A61K 31/00; A61K 31/352; A61K 31/717; A61K 35/17; A61K 35/37; A61K 36/27; A61K 36/37; A61K 36/605; A61K 39/02; A61K 47/36; A61K 47/6903; A61K 9/06; A61K 9/2833; A61K 9/48; A61K 9/4808; A61K 9/4875; A61K 9/4891; A61K 9/5036; A61P 13/12; A61P 1/10; A61P 43/00; A61P 37/00; A61P 1/00; A61P 29/00; A61P 35/00; A61P 1/14; A61P 19/10; A61P 1/04; A61P 31/04; A61P 3/00; A61P 3/04; A61P 17/00; A61P 17/16;
(Continued)

(56) References Cited
U.S. PATENT DOCUMENTS
2015/0283187 A1  10/2015 Sawada et al.

FOREIGN PATENT DOCUMENTS
JP     9-2959 A     1/1997
JP  2007-507526 A   3/2007
(Continued)

OTHER PUBLICATIONS

Arboleya et al, "Gut Bifidobcteria Populatins in Human Health and Aging", frontiers in Microbio. Mini Rev. vol. 7, Art. 1204. (Year: 2016).*
Jens Walter "Ecological Role of Lactobacilli in the Gastrin. Tract: Implications for Fundamental and Biomed. Res.", Applied Microbiol. 74(16) 4985-4996. (Year: 2008).*
(Continued)

*Primary Examiner* — Taeyoon Kim
*Assistant Examiner* — Tiffany M Gough
(74) *Attorney, Agent, or Firm* — Knobbe, Martens, Olson & Bear, LLP

(57) ABSTRACT

Provided is an agent having an action on a transcellular ion transporter in the intestinal tract, the agent containing a bacterium of the genus *Bifidobacterium* or the genus *Lactobacillus*, or a treated product thereof, with the proviso that the case where the ion transporter is a chloride channel and the action is inhibition; the case where the ion transporter is $Na^+K^+Cl^-$ cotransporter (NKCC1) and the action is inhibition; the case where the bacterium is *Bifidobacterium infantis* 35624; and the case where the bacterium is *Lactobacillus salivarius* UCC118 are excluded. The agent of the present invention is useful in activation of chloride channels, prevention or treatment of renal diseases, and/or promotion of defecation, and therefore, usable as a medicament, a supplement, etc.

11 Claims, 5 Drawing Sheets

(51) Int. Cl.
*A61P 13/12* (2006.01)
*A61K 35/747* (2015.01)
*C12N 1/20* (2006.01)

(58) Field of Classification Search
CPC .......... A61P 31/12; A61P 35/02; A61P 37/02; A61P 3/06; A61P 3/14; A61P 11/02; A61P 1/12; A61P 31/00; A61P 37/04; A61P 37/08; C12N 1/20; C12N 1/205; C12N 9/14; C12R 1/01; C12R 2001/01; Y02A 50/30; A23V 2002/00; A23V 2200/3204; C07K 16/00; C07K 5/0806; C07K 5/0812; C07K 5/1016; C07K 5/1024; C07K 7/06; C07K 7/08; C07K 16/2818; C07K 16/2827; A61Q 19/007; A61Q 17/005; A61Q 19/00; A61Q 19/005; A23L 29/262; A23L 33/24; A23L 21/00; A23L 29/30; A23L 33/105; A23L 33/21; A23L 5/00; A23L 7/00; C12P 19/04; C12P 1/04; C12P 1/689; G01N 33/56911; Y02E 50/10; Y02E 50/16
See application file for complete search history.

(56) References Cited

FOREIGN PATENT DOCUMENTS

| JP | 2008-517014 A | 5/2008 |
| JP | 4786866 B2 | 10/2011 |
| JP | 2014-101282 A | 6/2014 |
| WO | WO 03/030912 A1 | 4/2003 |
| WO | WO 2005/032591 A1 | 4/2005 |
| WO | WO 2006/045473 A1 | 5/2006 |
| WO | WO 2010/126073 A1 | 11/2010 |
| WO | WO 2015/112083 A1 | 7/2015 |

OTHER PUBLICATIONS

Lomasney et al., Converging effects of a Bifidobacterium and Lactobacillus probiotic strain on mouse intestinal physiology, American Journal Physiology Gastrointestinal Liver Physiology vol. 307: G241-G247. (Year: 2014).*
Guida et al., Effect of short-term synbiotic treatment on plasma p-cresol levels in patients with chronic renal failure: A randomized clinical trial, Nutrition, Metabolism and Cardiovascular Diseases, vol. 24, Issue 9, pp. 1043-1049. (Year: 2014).*
Kumar et al., Probiotic Bifidobacterium species stimulate human SLC26A3 gene function and expression in intestinal epithelial cells American Journal of Physiology and Cell Physiology ;307(12), p. C1084-92. (Year: 2014).*
Ranganathan et al., Pilot study of probiotic dietary supplementation for promoting healthy kidney function in patients with chronic kidney disease, Advances in Therapy vol. 27, pp. 634-647. (Year: 2010).*
Borthakur et al., The probiotic Lactobacillus acidophilus stimulates chloride/hydroxyl exchange activity in human intestinal epithelial cells, Journal of Nutrition, 38 vol. 7, p. 1355-1359. (Year: 2008).*
Raheja et al., Lactobacillus acidophilus stimulates the expression of SLC26A3 via a transcriptional mechanism, American Journal of Physiology—Gastrointestinal and Liver Physiology, vol. 298, G395-G401. (Year: 2010).*
International Preliminary Report on Patentability for PCT/JP2017/037698 dated Apr. 23, 2019.
Amagase, Harunobu "Current Marketplace for Probiotics: A Japanese Perspective" Clinical Infectious Diseases, 2008, pp. S73-S75, vol. 46 (Suppl 2).
International Search Report for PCT/JP2017/037698 dated Dec. 26, 2017.
Mattarelli et al., "Proposal to reclassify the three biotypes of Bifidobacterium longum as three subspecies: *Bifidobacterium longum* subsp. *Longum* subsp. Nov., *Bifidobacterium longum* subsp. *Infantis* comb nov. and *bifidobacterim longum* subsp. *Suis comb.* Nov." International Journal of Systematic and Evolutionary Microbiology (2008), 58, 767-772.
Science of lactic acid bacteria and bifidobacteria, 2010, 92, Japan Society for Lactic Acid Bacteria, Kyoto, Japan.

* cited by examiner

| | Age in weeks | | | | | | | 12 days | |
|---|---|---|---|---|---|---|---|---|---|
| | 6w | 7w | 8w | 9w | 10w | 11w | 12w | | |
| Normal | Preliminary breeding | CE-2 | | | | | | CE-2 + Test sample Oral administration (12 days) | Dissection |
| renal failure(RF) | | Mixed feed CE-2 containing 0.2% adenine | | | | | | | |
| RF+8013E(1) | | | | | | | | | |
| RF+8013E(10) | | | | | | | | | |

AGENT ACTING ON TRANSCELLULAR ION TRANSPORTER IN INTESTINAL TRACT, AGENT FOR ACTIVATING CHLORIDE CHANNEL, AGENT FOR PREVENTING OR TREATING RENAL DISEASE, OR AGENT FOR PROMOTING DEFECATION

CROSS REFERENCE TO RELATED APPLICATIONS

This application is a U.S. National Phase Application of PCT International Application Number PCT/JP2017/037698, filed on Oct. 18, 2017, designating the United States of America and published in the Japanese language, which is an International Application of and claims the benefit of priority to Japanese Patent Application No. 2016-206422, filed on Oct. 20, 2016. The disclosures of the above-referenced applications are hereby expressly incorporated by reference in their entireties.

TECHNICAL FIELD

The present invention relates to an agent acting on a transcellular ion transporter in the intestinal tract, an agent for activating a chloride channel, an agent for preventing or treating a renal disease, or an agent for promoting defecation, containing a certain bacterium or a treated product thereof.

BACKGROUND ART

A chloride ion ($Cl^-$), a calcium ion ($Ca^{2+}$), a sodium ion ($Na^+$), a potassium ion ($K^+$), etc. are known to be responsible for water/electrolyte transport, secretion, cell volume regulation, or the like, and also are known to play an important role as a factor influencing cellular responses. For example, a chloride channel is an ion-transport membrane protein for transporting chloride ions. It has been reported that various kinds of transcellular ion transporters are present in the cell membranes of nerves, muscles, and epithelia, and are involved in various physiological functions and cellular defense mechanisms.

In the intestinal tract, chloride ions are deeply involved in pathological conditions, such as diarrhea and constipation, and examples of diseases caused by disturbances in chloride ion balance include intractable constipation, paramyotonia atrophy, diseases accompanied with hypercalciuria such as renal calculus, anxiety, insomnia, cystic fibrosis, epilepsy, insensitivity, asthma, bronchitis, neuropathy, etc. (Patent Literature 1).

Meanwhile, the bacterial cells of *Lactobacillus gasseri*, a treated product thereof, and a mixture thereof are known to inhibit chloride channels in the large intestine, resulting in inhibition of moisture secretion and thus decrease in the moisture content in the intestinal tract (Patent Literature 2). However, there have been no reports on bacteria or the like that activate chloride channels so far.

CITATION LIST

Patent Literature

Patent Literature 1: Japanese Patent No. 4786866
Patent Literature 2: JP 2014-101282 A

SUMMARY OF INVENTION

Technical Problem

An object of the present invention is to provide a novel agent acting on a transcellular ion transporter in the intestinal tract, a novel agent for activating a chloride channel, a novel agent for preventing or treating a renal disease, or a novel agent for promoting defecation. Another object of the present invention is to provide a novel treated bacterial product having an ability to act on a transcellular ion transporter in the intestinal tract, an ability to activate a chloride channel, an effect of preventing or treating a renal disease, or an ability to promote defecation; and a method for producing the treated bacterial product.

Solution to Problem

The present inventors conducted research to achieve the above-mentioned objects, and as a result, found that certain bacteria or a treated product thereof acts on a transcellular ion transporter in the intestinal tract, activates a chloride channel, is effective in preventing or treating a renal disease, or has an ability to promote defecation. The present inventors conducted further examination, gained various novel findings, and completed the present invention.

That is, the present invention relates to the following.

(1) An agent having an action on a transcellular ion transporter in the intestinal tract, the agent containing a bacterium of the genus *Bifidobacterium* or the genus *Lactobacillus*, or a treated product thereof, with the proviso that the case where the ion transporter is a chloride channel and the action is inhibition; the case where the ion transporter is $Na^+K^+Cl^-$ cotransporter (NKCC1) and the action is inhibition; the case where the bacterium is *Bifidobacterium infantis* 35624; and the case where the bacterium is *Lactobacillus salivarius* UCC118 are excluded.

(2) The agent according to the above (1), wherein the action on the transcellular ion transporter is activation of a chloride channel.

(3) The agent according to the above (1) or (2), which is an agent for promoting defecation.

(4) An agent for preventing or treating a renal disease, containing a bacterium of the genus *Bifidobacterium* or the genus *Lactobacillus*, or a treated product thereof, with the proviso that the treated product does not contain any bacterial fermentation metabolite and that dogs and cats are excluded from subjects of administration.

(5) The agent according to any one of the above (1) to (4), wherein the bacterium of the genus *Bifidobacterium* is *Bifidobacterium longum*, *Bifidobacterium bifidum*, *Bifidobacterium breve*, *Bifidobacterium adolescentis*, *Bifidobacterium infantis*, *Bifidobacterium pseudolongum*, or *Bifidobacterium thermophilum*.

(6) The agent according to any one of the above (1) to (5), wherein the bacterium of the genus *Bifidobacterium* is *Bifidobacterium longum* CLA8013 (Accession Number: NITE BP-02352) or *Bifidobacterium longum* MM-2 (Accession Number: NITE BP-818).

(7) The agent according to any one of the above (1) to (6), wherein the bacterium of the genus *Lactobacillus* is *Lactobacillus acidophilus*, *Lactobacillus johnsonii*, *Lactobacillus gasseri*, *Lactobacillus casei*, *Lactobacillus plantarum*, *Lactobacillus delbrueckii* subsp. *bulgaricus*, *Lactobacillus delbrueckii* subsp. *lactis*, *Lactobacillus fermentum*, *Lactobacillus helveticus*, *Lactobacillus paracasei* subsp. *paracasei*,

*Lactobacillus reuteri, Lactobacillus rhamnosus, Lactobacillus salivarius*, or *Lactobacillus brevis*.

(8) The agent according to any one of the above (1) to (6), wherein the bacterium of the genus *Lactobacillus* is *Lactobacillus acidophilus* JCM1132, *Lactobacillus johnsonii* JCM2012, or *Lactobacillus gasseri* JCM5813.

(9) *Bifidobacterium longum* CLA8013 (Accession Number: NITE BP-02352).

(10) A method for producing a treated bacterial product of the genus *Bifidobacterium* or the genus *Lactobacillus*, the method comprising the steps of suspending bacterial cells in a sugar-free solvent (excluding purified water and physiological saline) or in a solvent containing Dulbecco's Modified Eagle Medium (DMEM) and Ham's F-12 to give a bacterial suspension;

leaving the bacterial suspension under anaerobic conditions; and subsequently filtering the supernatant of the bacterial suspension to give a filtrate as a treated product;

and not comprising any fermentation step.

(11) A supernatant of a suspension containing a bacterium of the genus *Bifidobacterium* or the genus *Lactobacillus* and a sugar-free solvent (excluding purified water and physiological saline) or a solvent containing DMEM and Ham's F-12, with the proviso that the supernatant does not contain the bacterium of the genus *Bifidobacterium* or the genus *Lactobacillus*.

Advantageous Effects of Invention

The present invention provides a novel agent having an action on a transcellular ion transporter in the intestinal tract. The agent of the present invention has a particularly significant effect in activation of chloride channels, prevention or treatment of renal diseases, or an ability to promote defecation.

DESCRIPTION OF EMBODIMENTS

Figure 1:
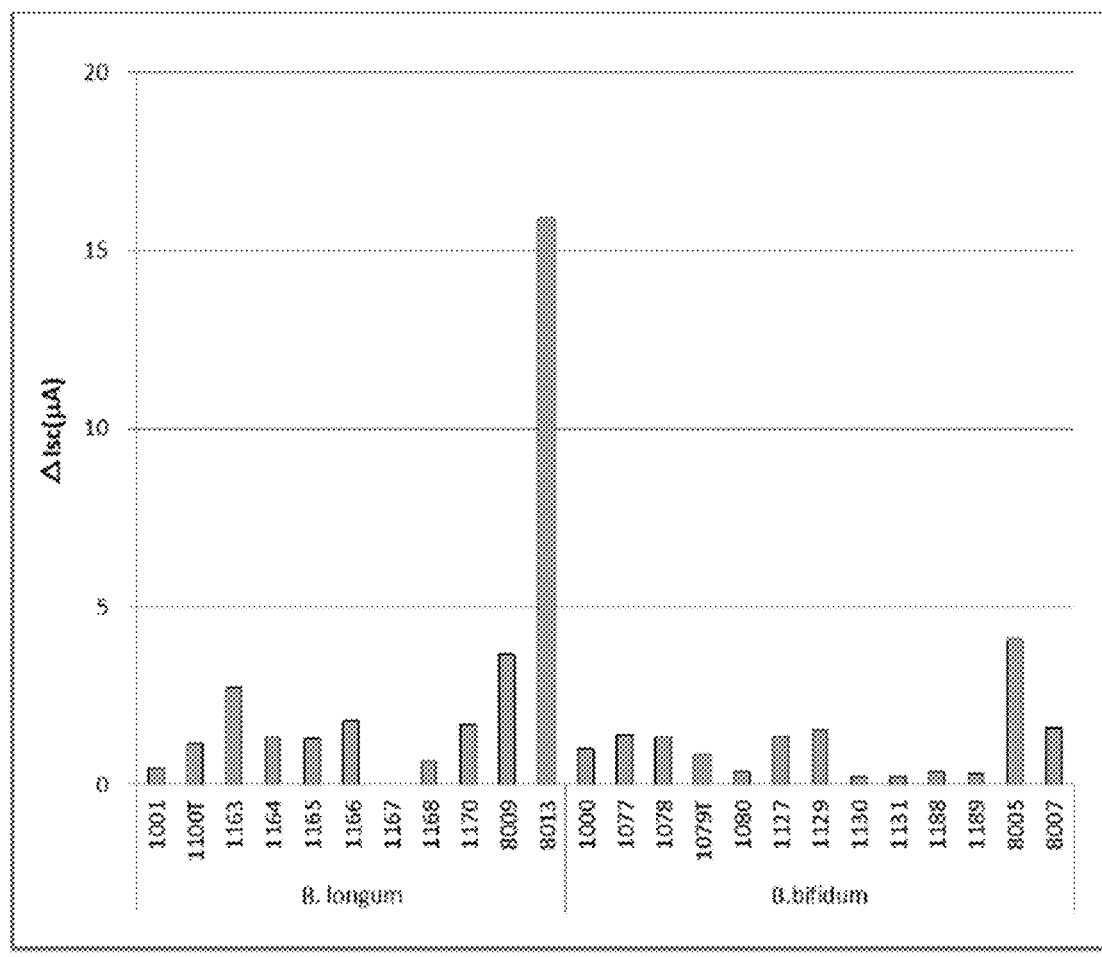
FIG. 1 is a graph showing short-circuit current changes in T84 intestinal epithelium cells in the presence of treated products of bacteria of the genus *Bifidobacterium*.

The present invention provides an agent having an action on a transcellular ion transporter in the intestinal tract, the agent containing a bacterium of the genus *Bifidobacterium* or the genus *Lactobacillus*, or a treated product thereof. Specifically, the present invention provides, for example, an agent for activating a chloride channel, an agent for preventing or treating a renal disease, or an agent for promoting defecation. The agent of the present invention has only to contain the above-mentioned lactic acid bacterium or a treated product thereof, and may further contain another component. As the bacterium, one species may be used alone, and also a mixture of two species or more may be used.

The agent of the present invention contains a bacterium of the genus *Bifidobacterium* or the genus *Lactobacillus*. As the lactic acid bacterium of the genus *Bifidobacterium*, preferred are *Bifidobacterium longum*, *Bifidobacterium bifidum*, *Bifidobacterium breve*, *Bifidobacterium adolescentis*, *Bifidobacterium infantis*, *Bifidobacterium pseudolongum*, *Bifidobacterium thermophilum*, etc., and among these, more preferred is *Bifidobacterium longum* or *Bifidobacterium bifidum*. As the *Bifidobacterium longum* or *Bifidobacterium bifidum*, preferred is *Bifidobacterium longum* CLA8013 (Accession Number: NITE BP-02352), *Bifidobacterium longum* ID8009, *Bifidobacterium longum* ID1163, *Bifidobacterium longum* MM-2: ID1001 (Accession Number: NITE BP-818), or *Bifidobacterium bifidum* ID8005, and more preferred is *Bifidobacterium longum* CLA8013 (Accession Number: NITE BP-02352) or *Bifidobacterium longum* MM-2: ID1001 (Accession Number: NITE BP-818). As the lactic acid bacterium of the genus *Lactobacillus*, preferred are *Lactobacillus acidophilus*, *Lactobacillus johnsonii*, *Lactobacillus gasseri*, *Lactobacillus casei*, *Lactobacillus plantarum*, *Lactobacillus delbrueckii* subsp. *bulgaricus*, *Lactobacillus delbrueckii* subsp. *lactis*, *Lactobacillus fermentum*, *Lactobacillus helveticus*, *Lactobacillus paracasei* subsp. *paracasei*, *Lactobacillus reuteri*, *Lactobacillus rhamnosus*, *Lactobacillus salivarius*, *Lactobacillus brevis*, etc., and among these, more preferred is *Lactobacillus acidophilus*, *Lactobacillus gasseri*, or *Lactobacillus johnsonii*. As the *Lactobacillus acidophilus*, *Lactobacillus gasseri*, or *Lactobacillus johnsonii*, preferred is *Lactobacillus acidophilus* JCM1132 (ID2152$^T$), *Lactobacillus gasseri* JCM5813 (ID2145), or *Lactobacillus johnsonii* JCM2012 (ID2153$^T$), and more preferred is *Lactobacillus acidophilus* JCM1132 (ID2152$^T$).

These bacterial cells are readily available from ATCC, IFO, and other organizations, or Japan Bifidus Foundation and other foundations. *Bifidobacterium longum* CLA8013 and *Bifidobacterium longum* MM-2 are deposited in Incorporated Administrative Agency National Institute of Technology and Evaluation, NITE Patent Microorganisms Depositary (Room 122, 2-5-8 Kazusakamatari, Kisarazu-shi, Chiba 292-0818 Japan) under the Accession Numbers shown below. Commercially available bacterial cells may also be used as appropriate.

*Bifidobacterium longum* CLA8013 (deposited on Sep. 21, 2016, under the Accession Number of NITE BP-02352)

*Bifidobacterium longum* MM-2 (deposited on Sep. 17, 2009, under the Accession Number of NITE BP-818)

The agent of the present invention contains neither *Bifidobacterium infantis* 35624 nor *Lactobacillus salivarius* UCC118.

The agent of the present invention may also contain useful bacteria other than the above-mentioned lactic acid bacteria. Examples of the useful bacteria include saccharifying bacteria, such as *Bacillus subtilis* including *Bacillus subtilis* 129 BIO H(α), *Bacillus mesentericus*, and *Bacillus polyfermenticus*; spore forming lactic acid bacteria, such as *Bacillus coagulans*; butyric acid bacteria, such as *Bacillus toyoi*, *Bacillus licheniformis*, and *Clostridium butyricum*; lactic acid cocci, such as the genus *Leuconostoc* including *Leuconostoc mesenteroides*, the genus *Lactococcus* including *Lactococcus lactis* and *Lactococcus cremoris*, the genus

*Tetragenococcus* including *Tetragenococcus halophilus*, the genus *Pediococcus* including *Pediococcus acidilactici* and *Pediococcus pentosaceus*, the genus *Oenococcus* including *Oenococcus oeni*; and others.

These bacterial cells are readily available from ATCC, IFO, and other organizations. Commercially available bacterial cells may also be used as appropriate.

The above-mentioned bacterial cells can be obtained by culture under publicly known conditions or similar conditions. For example, usually one or more kinds of the above-mentioned lactic acid bacteria are cultured in a fluid culture medium containing glucose, yeast extract, peptone, etc. aerobically or anaerobically at about 25 to 45° C. for about 4 to 72 hours. By cell collection from the culture fluid and subsequent washing, wet bacterial cells are obtained.

The bacteria used in the present invention are preferably viable cells, but may be killed cells, for example, in a dried form (dried bacterial cell product) or the like, and may also be a mixture of viable cells and killed cells etc. The dried bacterial cell product is preferably a single micron-sized dried bacterial cell product. The dried bacterial cell product usually means individual dried bacterial cells or an aggregate of dried bacterial cells. The "single micron" means a size which is rounded to 1 to 10 μm by rounding to the nearest whole number.

In the present invention, the treated bacterial product means a bacterial product obtained by treating bacteria in some way, and the treatment is not particularly limited. The treated bacterial product may be, for example, a liquid mixture of the bacterial cells and a solvent, a supernatant or centrifugation supernatant thereof, a filtrate obtained by filtering the liquid mixture or the supernatant using a filter or the like, etc. The liquid mixture of bacterial cells and a solvent may be a suspension as long as the bacterial cells and the solvent are mixed. The liquid mixture may be used immediately after the mixing, or after being left to stand, for example, at about 25 to 45° C. for about 30 minutes to about 3 days under aerobic or anaerobic conditions. The treated bacterial product may also be an extract or the like therefrom. In the present invention, such a treated bacterial product may be written simply as an extract. The treated bacterial product may also be a product obtained by, for example, concentrating, powderizing, or lyophilizing the filtrate, extract, or the liquid mixture according to the known technique. The treated bacterial product of the present invention does not contain any bacterial fermentation metabolite. Examples of the solvent include a sugar-free solvent, such as phosphate buffer (PBS); a culture medium, such as DMEM/F-12; etc. The phosphate buffer (PBS) may be a phosphate buffer with calcium and magnesium salts (PBS (+)) or a phosphate buffer without calcium and magnesium salts (PBS (−)). The centrifugation conditions are not particularly limited, and the centrifugal force may be 2,500 to 10,000×G. The size of the opening of the filter is not particularly limited as long as the filter is usable for filtering bacteria, and for example, a commercially available filter of 0.1 μm to 1 μm (for example, 0.22 μm) may be used. The culture medium, such as DMEM/F-12, may contain sugars but does not need to contain sugars. The solvent of the present invention does not include purified water or physiological saline.

In the present invention, the bacterial fermentation metabolite means, for example, a bacterial fermentation metabolite in the form of a liquid obtained by seeding a bacterium in a bacterial growth medium containing skim milk powder, lactose, glucose, peptone, a yeast extract, etc., and subsequent culturing at a certain temperature (for example, 20° C. to 40° C.) for a certain period of time (for example, 2 to 60 hours).

The treated bacterial product of the present invention may be a product containing or not containing bacterial cells, but preferably is a product not containing bacterial cells. However, this does not apply to a treated bacterial product of the present invention prepared without bacterial fermentation.

In the present invention, the intestinal tract may be the small intestine, such as the duodenum, the jejunum, the ileum, or the like; the large intestine, such as the cecum, the ascending colon, the transverse colon, the descending colon, the sigmoid colon, the rectum, or the like; etc. Furthermore, in the present invention, the intestinal tract may be kept inside the body, cut out of the body, or partly taken out of the body through an abdominal incision.

In the present invention, the transcellular ion transporter means an entity that transports ions through cells, and is also referred to as a transcellular ion-transporting entity. Examples of the ion transporter include an ion channel, an ion cotransporter, an ion exchanger, etc. Examples of the ion channel include a chloride channel, a calcium channel, a sodium channel, a potassium channel, a cation channel, etc. Examples of the chloride channel include a CFTR chloride channel etc. Examples of the ion cotransporter include $Na^+K^+Cl^-$ cotransporter (NKCC1) etc. Examples of the ion exchanger include a $Cl^-/HCO_3^-$ exchanger (DRA) etc.

In the present invention, "having an action on a transcellular ion transporter" means altering the function of the transcellular ion transporter, for example, activating or inhibiting the function. It specifically means activating a chloride channel, activating a calcium channel, activating a sodium channel, activating a potassium channel, activating a cation channel, activating $Na^+K^+Cl^-$ cotransporter (NKCC1), activating a $Cl^-/HCO_3^-$ exchanger (DRA), etc. Also, it specifically means inhibiting a calcium channel, inhibiting a sodium channel, inhibiting a potassium channel, inhibiting a cation channel, inhibiting a $Cl^-/HCO_3^-$ exchanger (DRA), etc.

However, the present invention does not include the case where the ion transporter is a chloride channel and the action is inhibition; the case where the ion transporter is $Na^+K^+Cl^-$ cotransporter (NKCC1) and the action is inhibition; the case where the bacterium is *Bifidobacterium infantis* 35624; or the case where the bacterium is *Lactobacillus salivarius* UCC118.

Hereinafter, each aspect of the agent of the present invention having an action on a transcellular ion transporter in the intestinal tract will be described. Specifically, an agent for activating a chloride channel, an agent for preventing or treating a renal disease, and an agent for promoting defecation will be described.

An embodiment of the present invention is, for example, an agent for activating a chloride channel. In the present invention, activation of a chloride channel means, for example, increase of the ability for transcellular ion transport as compared with that before the administration of the agent of the present invention. The ability for transcellular ion transport can be measured by, for example, the short-circuit current technique (Shinichiro Karaki and Atsukazu Kuwahara, Electrophysiological measurement of transepithelial ion transport: short-circuit current technique, *Folia Pharmacol. Jpn.*, 123, 211-218, 2004).

An embodiment of the present invention is, for example, an agent for preventing or treating a renal disease. In the present invention, the agent for preventing or treating a renal disease is useful for preventing or treating a renal disease. In the present invention, "prevention" of a renal disease means, for example, prevention of development of a renal disease by acting on a transcellular ion transporter in the intestinal tract, for example, on an ion channel, and "treatment" of a renal disease means, for example, remission of symptoms accompanied with a renal disease or cure of the disease. Examples of the renal disease include renal failure, uremia, diabetic nephropathy, chronic glomerulonephritis, etc. The renal disease may be chronic or acute, for example. Examples of the chronic renal disease include chronic renal failure, chronic glomerulonephritis, diabetic nephropathy, nephrotic syndrome, etc. Examples of the acute renal disease include acute glomerulonephritis, acute renal failure, hemolytic uremic syndrome, etc.

In the present invention, the method for judging the improvement in a renal disease is not particularly limited, and the improvement may be judged by a publicly known method etc. Examples of the method for judging the improvement in a renal disease as a result of the administration of a bacterium or a treated product thereof in the present invention or the administration of the agent of the present invention include a method involving blood urea nitrogen (BUN) measurement etc. In the cases where the method involving BUN measurement is used, when BUN is decreased than that before the administration of a bacterium, a treated bacterial product, or an agent, for example, it may be judged that the bacterium, the treated bacterial product, or the agent has an improving effect on the renal disease.

An embodiment of the present invention is, for example, an agent for promoting defecation. The agent of the present invention has an action of activating a chloride channel, thereby increasing the moisture content in the intestinal tract, and gaining an ability to promote defecation.

In the present invention, the agent for promoting defecation can, for example, promote physiological defecation or shorten the time from food intake to defecation.

In the present invention, the method for judging the effectiveness in promoting defecation is not particularly limited, and for example, the effectiveness can be judged based on defecation frequency, the time from food intake to defecation, or the moisture content in feces.

The agent of the present invention, which contains bacteria or a treated product thereof alone or a mixture of the bacteria or the treated product and other components can be used as a raw material for the production of a pharmaceutical product, a quasi-pharmaceutical product, a food or drink, a food additive, a feed, or the like; or directly used in the form of a pharmaceutical product, a quasi-pharmaceutical product, a food or drink, a food additive, a feed, or the like. The composition of the present invention does not need to contain coenzyme $Q_{10}$. That is, a pharmaceutical composition, a quasi-pharmaceutical composition, a food or drink composition, a food additive composition, a feed composition, or the like is an aspect of the present invention. A pharmaceutical composition containing the agent of the present invention is also one of the preferred embodiments of the present invention.

The dosage form of the pharmaceutical composition of the present invention may be determined as appropriate for administration in consideration of the physicochemical and biological properties of each component, etc. The pharmaceutical composition is suitable for oral administration, and is preferably in the form of an internal agent. The dosage form of the pharmaceutical composition of the present invention may also be a parenteral preparation. Examples of the dosage form of the internal agent include solid preparations, such as a tablet (including a sugar-coated tablet), a pellet, a fine granule, a powder, a granule, a pill, a chewable tablet, a troche, and a capsule; liquid preparations, such as a solution, a suspension, an emulsion, a syrup, and an elixir; and semi-solid preparations, such as a gel-like preparation; etc. Among them, a tablet, a powder, a liquid, or a suspension is preferred. Further, the pharmaceutical composition of the present invention may appropriately contain, in addition to lactic acid bacteria, publicly known additives or the like used in the art, such as an excipient (for example, saccharose, lactose, starch, crystalline cellulose, sodium phosphate, magnesium carbonate, pectin, dextrin, tragacanth, or the like), a binder (for example, starch, gelatin, carmellose sodium, methylcellulose, hydroxypropylmethylcellulose, hydroxypropylcellulose, polyvinyl pyrrolidone, pectin, tragacanth, or the like), a disintegrant (for example, starch, carmellose sodium, tragacanth, or the like), a lubricant (for example, talc, magnesium stearate, calcium stearate, macrogol, sucrose fatty acid ester, or the like), a stabilizer (sodium hydrogensulfite, sodium thiosulfate, sodium edetate, sodium citrate, ascorbic acid, dibutyl hydroxytoluene, or the like), a thickener (sodium carboxymethylcellulose or the like), a carrier (a low-melting-point wax, cacao butter, or the like), a colorant, a flavoring agent (flavor), a brightener, a diluent, a buffer, an emulsifier, a dispersant, a suspending agent, an antiseptic, an absorption enhancer, a corrigent, or the like. The total amount of the bacteria or a treated product thereof in the whole final preparation is usually selected as appropriate from the range of about 0.000001 to 99% by mass. The amount is preferably about 0.05 to about 50% by mass, and more preferably about 0.1 to about 25% by mass.

In the present invention, oral solid preparations (a tablet (including a sugar-coated tablet), a pill, a capsule, a powder, a granule, or the like) are preferred, which can be formulated by mixing an active ingredient with an additive, for example, an excipient (lactose, mannitol, glucose, microcrystalline cellulose, starch, or the like), a binder (hydroxypropylcellulose, polyvinyl pyrrolidone, magnesium aluminometasilicate, or the like), a disintegrant (calcium cellulose glycolate, or the like), a lubricant (magnesium stearate, or the like), a stabilizer, a solubilizer (glutamic acid, aspartic acid, or the like), or the like, according to a conventional method. As needed, such preparations may be further coated with a coating agent (saccharose, gelatin, hydroxypropylcellulose, hydroxypropylmethylcellulose phthalate, or the like), and the coating may consist of two or more layers.

In the cases where the agent of the present invention is used in the form of a solid preparation, depending on the drying method, powders may be simply mixed or compressed into a granule or a tablet. In the cases where a wet method is employed to obtain a granule or a tablet, kneading with use of a solution as a binder and drying are performed to give an intended solid preparation. Further, a powder or a granule obtained as above may be encapsulated to give a capsule.

For example, to prepare a tablet, a publicly known tableting machine is preferably used. Examples of the tableting machine include a single punch tableting machine and a rotary tableting machine. Also, a pill, a chewable tablet, or a troche may be prepared according to a publicly known method, for example, by the same means as that for tablet preparation.

In order to obtain a uniform mixture by mixing a slight amount of an active ingredient (bacteria or a treated product thereof) with a large amount of another powder, the so-called gradual mixing method is preferably employed. For example, by well mixing the active ingredient with 100 to 200 times its volume of another powder and subsequently mixing the obtained uniform powder mixture with the remaining powder, a uniformly diluted powder mixture can be obtained.

To dry an aqueous substance, spray drying, L-drying, freeze-drying, or other means can be used.

In the present invention, oral liquid preparations (a solution, a suspension, an emulsion, a syrup, an elixir, or the like) are formulated by dissolving, suspending, or emulsifying an active ingredient in a generally used diluent (purified water, ethanol, or a mixture thereof, or the like). The liquid preparation may further comprise a wetting agent, a suspending agent, an emulsifier, a sweetener, a flavor, a fragrance, a preservative, a buffer, or the like.

Examples of parenteral preparations include injections (for example, a subcutaneous injection, an intravenous injection, an intramuscular injection, and an intraperitoneal injection), an intravenous fluid, external preparations (for example, an intranasal preparation, a transdermal preparation, and an ointment), and suppositories (for example, an intrarectal suppository and an intravaginal suppository). These preparations can be formulated with use of a pharmaceutically acceptable additive as described above by a method conventionally used in the art. The total amount of the bacteria or a treated product thereof in the whole final preparation is usually selected as appropriate from the range of about 0.000001 to 99% by mass. The amount is preferably about 0.05 to about 50% by mass, and more preferably about 0.1 to about 25% by mass.

In the present invention, examples of the parenteral preparation include injections. The injections include a solution, a suspension, an emulsion, and a solid to be dissolved or suspended before use. The injections are formulated by dissolving, suspending, or emulsifying the active ingredient in a solvent. As the solvent, for example, distilled water for injection; physiological saline; a vegetable oil; alcohols, such as propylene glycol, polyethylene glycol, ethanol, and a combination thereof may be used. The injection may further comprise a stabilizer, a solubilizer (glutamic acid, aspartic acid, Polysorbate 80 (registered trademark), or the like), a suspending agent, an emulsifier, a soothing agent, a buffer, a preservative, or the like. These injections are sterilized in the final step or produced by aseptic manipulation. The injection may be produced in the form of a sterile solid preparation, for example a lyophilized product, which is dissolved in sterilized or sterile distilled water for injection or in another solvent just before use.

Other examples of the parenteral preparation include suppositories. This form of the composition may be produced by the usual method.

The bacteria used in the present invention are generally anaerobic and have a low tolerance for air or oxygen under dry conditions and for high temperature and moisture. Therefore, the preparation of such a composition is preferably performed in the presence of an inert gas or in vacuo at a low temperature. The temperature at the time of formulation of the composition is not particularly limited as long as the effect of the present invention is exerted, and can be selected according to a known method.

In the present invention, the dosage amount of the bacterium to an animal including a human, per adult per administration, is preferably about $1 \times 10^3$ to $1 \times 10^{11}$ cells, more preferably about $1 \times 10^6$ to $1 \times 10^{11}$ cells, and still more preferably about $1 \times 10^9$ to $1 \times 10^{11}$ cells.

In the present invention, the dosage amount of the treated bacterial product to an animal including a human, per adult per administration, is preferably an amount of the product obtained by treating about $1 \times 10^3$ to $1 \times 10^{14}$ bacterial cells, more preferably an amount of the product obtained by treating about $1 \times 10^6$ to $1 \times 10^{14}$ bacterial cells, and still more preferably an amount of the product obtained by treating about $1 \times 10^9$ to $1 \times 10^{14}$ bacterial cells.

In the present invention, the interval between uses of the composition varies depending on the subject (for example, a rat), the route (for example, oral administration), the dosage form (for example, a liquid), etc. The composition of the present invention may be used, for example, 1 to 5 times per day, 1 to 5 times per week, 1 to 5 times per month, etc.

In the present invention, the duration of use of the composition varies depending on the subject (for example, a mouse), the route (for example, oral administration), the dosage form (for example, a liquid), the interval between uses, etc. The composition of the present invention may be used, for example, for 1 day to 6 days, 1 week to 4 weeks, 1 month to 12 months, etc. Also, the composition may be continuously used, for example.

In the present invention, the subject of the administration of the agent may be, for example, an animal (for example, a human, a rat, a mouse, a rabbit, sheep, a pig, a cow, a cat, a dog, a monkey, etc.).

In the present invention, the subject of the administration of the agent for preventing or treating a renal disease is preferably an animal other than a dog or a cat (for example, a human, a rat, a mouse, a rabbit, sheep, a pig, a cow, a monkey, etc.).

Examples of the disease to which the pharmaceutical composition of the present invention can be applied include inflammatory bowel disease, ulcerative colitis, Crohn's disease, intestinal tuberculosis, infectious enteritis, noninfectious enteritis, acute enteritis, acute gastroenteritis, chronic enteritis, irritable bowel syndrome (IBS), colorectal cancer, ileus, constipation, nephritis, renal failure, nephrotic syndrome, diabetic nephropathy, glomerulonephritis, renal calculus, polycystic kidney, renal anemia, nephrosclerosis, hydronephrosis, etc.

The agent of the present invention may be used as a raw material of a composition other than a pharmaceutical composition, and such another composition can be produced using, for example, the above described bacteria or a treated product thereof, according to a known method. The amount of the bacteria or a treated product thereof in the whole composition other than a pharmaceutical composition is selected as appropriate from the range of about 0.000001 to 99% by mass, for example.

In the present invention, examples of the food or drink include a soft drink, a lactic drink, fermented milk, yogurt, a *lactobacillus* drink, a supplement, etc.

The present invention encompasses a method for producing a treated bacterial product of the genus *Bifidobacterium* or the genus *Lactobacillus*, the method comprising the steps of suspending bacterial cells in a sugar-free solvent (excluding purified water and physiological saline) or in a solvent containing DMEM and Ham's F-12 to give a bacterial suspension;

leaving the bacterial suspension under anaerobic conditions; and subsequently filtering the supernatant of the bacterial suspension to give a filtrate as a treated product;

and not comprising any fermentation step.

In the present invention, examples of the sugar-free solvent include a solution containing phosphoric acid, phosphate buffer (PBS), or the like, but does not include purified water or physiological saline. The solution containing phosphoric acid may be any solution containing at least phosphoric acid. The phosphate buffer (PBS) may be a phosphate buffer with calcium and magnesium salts (PBS(+)) or a phosphate buffer without calcium and magnesium salts (PBS(−)). For a higher ability for transcellular ion transport, PBS(−) is preferably used. Examples of the sugar include lactose, sucrose, oligosaccharide, sugar alcohol, etc.

In the present invention, the DMEM used may contain, for example, glycine, L-arginine hydrochloride, L-cystine dihydrochloride, L-glutamine, L-histidine monohydrochloride monohydrate, L-isoleucine, L-leucine, L-lysine monohydrochloride, L-methionine, L-phenylalanine, L-serine, L-threonine, L-tryptophan, L-tyrosine disodium hydrate, L-valine, calcium D-pantothenate, choline chloride, folic acid, i-inositol, nicotinamide, pyridoxine hydrochloride, riboflavin, thiamine hydrochloride, anhydrous calcium chloride, iron (III) nitrate enneahydrate, anhydrous magnesium sulfate, potassium chloride, sodium chloride, sodium hydrogencarbonate, anhydrous monobasic sodium phosphate, D-glucose, phenol red, etc.

In the present invention, the Ham's F-12 used may contain, for example, glycine, L-alanine, L-arginine hydrochloride, L-asparagine monohydrate, L-aspartic acid, L-cysteine hydrochloride monohydrate, L-glutamic acid, L-glutamine, L-histidine monohydrochloride monohydrate, L-isoleucine, L-leucine, L-lysine monohydrochloride, L-methionine, L-phenylalanine, L-proline, L-serine, L-threonine, L-tryptophan, L-tyrosine disodium hydrate, L-valine, biotin, choline chloride, calcium D-pantothenate, folic acid, nicotinamide, pyridoxine hydrochloride, riboflavin, thiamine hydrochloride, vitamin B12, i-inositol, anhydrous calcium chloride, copper (II) sulfate pentahydrate, iron (II) sulfate heptahydrate, potassium chloride, anhydrous magnesium chloride, sodium chloride, sodium hydrogencarbonate, anhydrous monobasic sodium phosphate, zinc sulfate heptahydrate, D-glucose, hypoxanthine, linoleic acid, lipoic acid, putrescine dihydrochloride, thymidine, phenol red, sodium pyruvate, etc.

In the present invention, examples of the solvent containing DMEM and Ham's F-12 include a mixed solvent of DMEM and Ham's F-12, a solution containing DMEM and Ham's F-12, a medium containing DMEM and Ham's F-12, etc.

In the present invention, the medium containing DMEM and Ham's F-12 used may be a mixture of commercial products or the like, an already mixed commercial product (DMEM/F-12 medium made by Thermo Fisher Scientific), a commercial sugar-free product, etc.

The DMEM/F-12 medium used in the present invention may be prepared by, for example, mixing components contained in a commercial product or the like, such as L-glutamine, phenol red, sodium pyruvate, anhydrous calcium chloride, potassium chloride, anhydrous magnesium chloride, anhydrous magnesium sulfate, sodium chloride, sodium hydrogencarbonate, disodium hydrogen phosphate anhydrous, anhydrous monobasic sodium phosphate, copper (II) sulfate pentahydrate, iron (III) nitrate enneahydrate, iron (II) sulfate heptahydrate, zinc sulfate heptahydrate, L-alanine, L-arginine hydrochloride, L-asparagine monohydrate, L-aspartic acid, L-cystine dihydrochloride, L-cysteine hydrochloride monohydrate, L-glutamic acid, L-glutamine, glycine, L-histidine monohydrochloride monohydrate, L-isoleucine, L-leucine, L-lysine monohydrochloride, L-methionine, L-phenylalanine, L-proline, L-serine, L-threonine, L-tryptophan, L-tyrosine disodium hydrate, L-valine, D-biotin, D-pantothenate, choline chloride, folic acid, i-inositol, nicotinamide, pyridoxine hydrochloride, riboflavin, thiamine hydrochloride, vitamin B12, D-glucose, hypoxanthine, linoleic acid, lipoic acid, putrescine dihydrochloride, thymidine, etc.

For convenience, use of a commercially available DMEM/F-12 medium is preferred.

In the present invention, "leaving under anaerobic conditions" means, for example, leaving in the conditions where the oxygen level in the headspace is reduced to zero by nitrogen replacement, or leaving in a culture tank where the dissolved oxygen (D. O.) level in the bacterial suspension is 1.0 ppm or less. Particularly preferably, a bacterial suspension is left to stand under anaerobic conditions where the dissolved oxygen (D. O.) level in the bacterial suspension is adjusted to 0.5 ppm or less by nitrogen replacement, but this is a non-limiting example.

In the present invention, "leaving a bacterial suspension" means, after mixing bacteria with a sugar-free solvent (excluding purified water and physiological saline) or a solvent containing DMEM and Ham's F-12, leaving the mixture to stand without any operation to the bacterial suspension and/or the container containing the bacterial suspension. The leaving time is not particularly limited, and may be, for example, 30 minutes or more, 1 hour or more, 6 hours or more, etc., and also may be 24 hours or less, 3 days or less, etc. The temperature at the time of leaving the bacterial suspension is not particularly limited as long as the temperature allows bacteria to grow. The conditions under which the bacterial suspension is left to stand depend on the nature of the bacteria, and may be aerobic conditions or anaerobic conditions, for example.

In the present invention, the filter is only required to be capable of filtering bacteria, and for example, a commercially available filter of 0.1 μm to 1 μm (for example, 0.22 μm) may be used.

In the present invention, steps of, for example, concentration, powderization, lyophilization, etc. of the treated product of a filtrate may further be comprised.

In the present invention, "not comprising any fermentation step" means, for example, that lactic acid fermentation does not occur, that the treated product obtained after all the production steps in the production method does not contain any metabolite resulting from lactic acid fermentation, etc.

In the present invention, the method for judging whether lactic acid fermentation has occurred is not particularly limited. For example, in the case where the pH of a prepared bacterial suspension measured after leaving the bacterial suspension is lower than that measured before the leaving (changed toward the acidic side), lactic acid fermentation is judged as having occurred, which is not within the scope of the present invention.

The present invention encompasses a method for activating a chloride channel, preventing or treating a renal disease, or promoting defecation, the method comprising administering, to an animal, a bacterium of the genus *Bifidobacterium* or the genus *Lactobacillus*, or a treated product thereof.

The present invention also encompasses use of a bacterium of the genus *Bifidobacterium* or the genus *Lactobacillus*, or a treated product thereof for the production of an agent for activating a chloride channel, an agent for preventing or treating a renal disease, or an agent for promoting defecation.

The present invention also encompasses a bacterium of the genus *Bifidobacterium* or the genus *Lactobacillus*, or a treated product thereof for use in activating a chloride channel, preventing or treating a renal disease, or promoting defecation.

The present invention also encompasses use of a bacterium of the genus *Bifidobacterium* or the genus *Lactobacillus*, or a treated product thereof for activating a chloride channel, preventing or treating a renal disease, or promoting defecation in an animal.

EXAMPLES

Hereinafter, the present invention will be illustrated in detail by Examples, but the technical scope of the present invention is not limited thereto. Various modifications can be made within the technical idea of the present invention by those with ordinary skill in the art.

Example 1 (Preparation of Treated Bacterial Product)

The bacteria of the genus *Bifidobacterium* or the genus *Lactobacillus* used are
*Bifidobacterium longum* (*B. longum*): ID1001 (MM-2, accession number: NITE BP-818), JCM1217 (ID1100$^T$), ID1163, ID1164, ID1165, ID1166, ID1167, ID1168, ID1170, ID8009, CLA8013 (accession number: NITEBP-02352),
*Bifidobacterium bifidum* (*B. bifidum*): ID1000, ID1077, ID1078, JCM1255 (ID1079$^T$), ID1080, ID1127, ID1129, ID1130, ID1131, ID1188, ID1189, ID8005, ID8007,
*Lactobacillus gasseri* (*L. gasseri*): ID2000, JCM1131 (ID2151$^T$), ID2089, ID2092, ID2093, ID2100, ID2101, ID2124, ID2144, JCM5813 (ID2145), ID2146,
*Lactobacillus johnsonii* (*L. johnsonii*): JCM2012 (ID2153$^T$), ID2091, ID2095, ID2096, ID2126, ID2142, ID2143, ID2154,
*Lactobacillus acidophilus* (*L. acidophilus*): JCM1132 (ID2152$^T$), ID2073, ID2107, ID2109, ID2110, and
*Lactobacillus paracasei* subspecies *paracasei* (*L. paracasei* subsp. *paracasei*): JCM8130 (ID2148$^T$), ID2003, ID2004, ID2005, ID2012, ID2013, ID2014, ID2019, ID2031, ID2032, ID2033. *B. longum* JCM1217 (ID1100$^T$), *B. bifidum* JCM1255 (ID1079$^T$), *L. gasseri* JCM5813 (ID2145), *L. gasseri* JCM1131 (ID2151$^T$), *L. johnsonii* JCM2012 (ID2153$^T$), *L. acidophilus* JCM1132 (ID2152$^T$), and *L. paracasei* subsp. *paracasei* JCM8130 (ID2148$^T$) are the standard strains of each species.

Cryopreserved cells of each strain (about $1\times10^6$ to $1\times10^8$ cells) were anaerobically cultured using 10 mL of GAM medium (Nissui Pharmaceutical) containing 1% glucose and 0.1% Polysorbate 80 at 37° C. for 18 to 30 hours. Subsequently, the culture was centrifuged (3,000×G, 10 min, R.T.) and the supernatant was discarded. The cells were washed with PBS(−), resuspended in 10 mL of DMEM/F-12 (made by Thermo Fisher Scientific), and left to stand under anaerobic conditions at 37° C. for 24 hours. After centrifugation, the supernatant was filtered through a filter (0.22 μm) to prepare the filtrate as a treated bacterial product (Extract: hereinafter may be abbreviated to E).
(Cell Culture)

A human colon epithelial cell line T84 was cultured in DMEM/F-12 containing 10% FBS and penicillin/streptomycin. The cells were seeded at $4\times10^4$ cells/cm$^2$, and passaged every 5 to 7 days. The cells were seeded at $5\times10^3$ cells/well on a filter Snapwell (Corning, Costar, 1.13 cm$^2$), and the medium was replaced every 3 days. After cultured for 5 to 7 days, the cells were used in the tests.
(Short-Circuit Current Technique)

For the measurement using short-circuit current technique, the Ussing chamber system (made by Physiologic Instruments) was used. The Snapwell having the T84 cells in the form of monolayer was vertically set in an Ussing chamber, and the left and right of the Snapwell having the attached T84 cells was filled with 5 mL of a Krebs-Ringer solution kept at 37° C. This was left to stand for 20 minutes or longer, and after the current value across the T84 cell membrane (Isc) was stabilized, the test was started. To the upper side as the mucosal side of the T84 cells (opposite side to the surface where cells adhered to the Snapwell), 100 μL of the treated bacterial product was added, and subsequent changes in the Isc (ΔIsc) was observed to compare changes in the transcellular ion secretion. ΔIsc was the maximum difference between the Isc value after the sample addition and the Isc value at the time of sample addition (0 hour).
(Ability of Treated Bacterial Product for Transcellular Ion Transport)

Figures 2, 3:
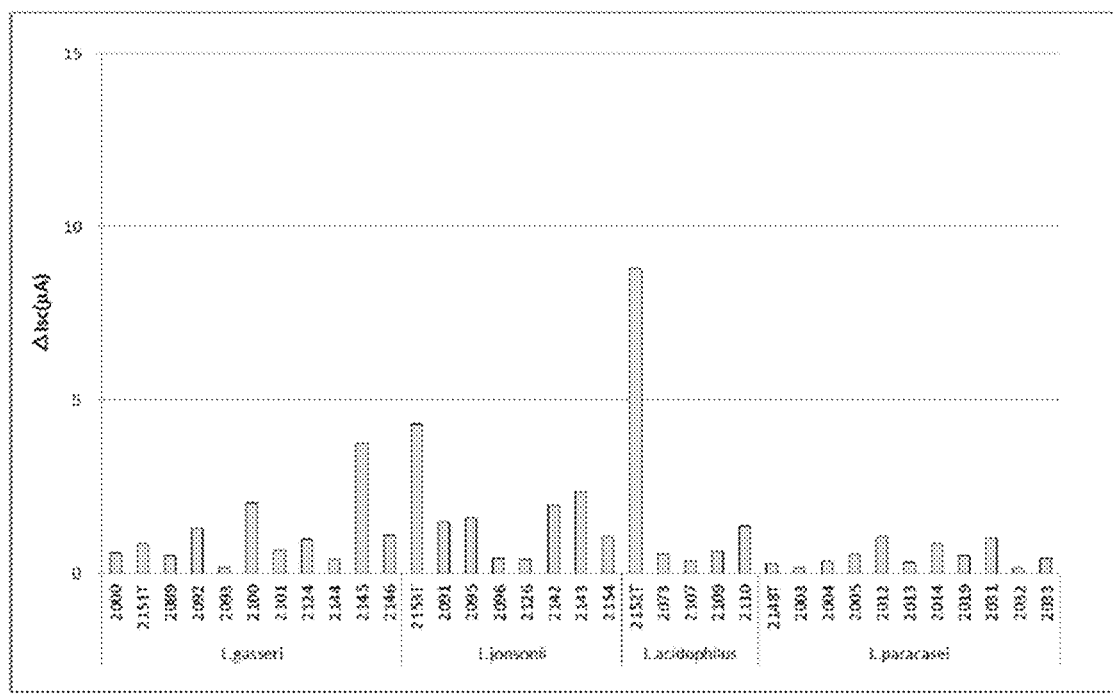
FIG. 2 is a graph showing short-circuit current changes in T84 intestinal epithelium cells in the presence of treated products of bacteria of the genus *Lactobacillus*.
FIG. 3 shows the test schedule for blood urea nitrogen (BUN) measurement.

The moisture content in the intestinal tract exerts influence on the hardness and movement of the intestinal content, and is one of the causes of constipation or diarrhea. Since secretion and absorption of water in the intestinal tract occurs in parallel to the movement of chloride ions through chloride channels present in the intestinal epithelium, the movement of chloride ions serves as an index of the movement of water. Therefore, using intestinal epithelium cells (T84 cells), the ability of bacteria for transcellular ion transport was examined by the short-circuit current technique with an Ussing chamber. The results of the ability of each treated bacterial product for transcellular ion transport measured by the short-circuit current technique using T84 cells are shown in FIG. 1 (*Bifidobacterium*) and FIG. 2 (*Lactobacillus*). The treated product of *B. longum* CLA8013 showed the maximum ΔIsc.

To the mucosal side of the T84 cells, 10 mM (dissolved in DMSO) CFTRinh172 (Sigma C992-25MG), which is a chloride channel inhibitor, in a Krebs-Ringer solution (5 μL/5 mL, final concentration: 10 μM) was applied, and after 2 minutes, 100 μL of the treated product of *B. longum* CLA8013 was added to the mucosal side of the T84 cells. While the ΔIsc of the treated bacterial product of *B. longum* CLA8013 without CFTRinh172 treatment (treated with DMSO) was 11.38 μA, the ΔIsc of the treated bacterial product of *B. longum* CLA8013 with CFTRinh172 treatment was 3.50 μA. That is, the chloride channel inhibitor decreased the ability of the treated bacterial product of *B. longum* CLA8013. The results showed that the treated bacterial product of *B. longum* CLA8013 activated chloride channels in the intestinal tract. Consequently, it was also shown that the treated bacterial product of *B. longum* CLA8013, which is capable of activating chloride channels, has an ability to promote water secretion and thereby promote defecation.

Example 2 (Preparation of Treated Bacterial Product)

Preparation Method of Treated Product of Bacteria (*Bifidobacterium longum* CLA8013)

Cryopreserved cells of *B. longum* CLA8013 (about $1\times10^8$ cells) were anaerobically cultured using 10 mL of GAM medium (Nissui Pharmaceutical) containing 1% glucose and 0.1% Polysorbate 80 at 37° C. for 30 hours. Subsequently, the culture was centrifuged (3,000×G, 10 min, R.T.) and the supernatant was discarded. The cells were washed with PBS(−), resuspended in 10 mL of PBS(−), and left to stand under anaerobic conditions at 37° C. for 24 hours. After centrifugation, the supernatant was filtered through a filter (0.22 μm) to prepare the filtrate as a treated product (8013E)

of bacteria (*B. longum* CLA8013). A dilution obtained by diluting the 8013E with PBS(−) so as to have an absorbance of 33 at 260 nm was referred to as 8013E(10), and a dilution obtained by diluting the 8013E with PBS(−) so as to have an absorbance of 3.3 at 260 nm was referred to as 8013E(1).
(Improving Ability of Treated Product of Bacteria (*B. longum* CLA8013) in Chronic Renal Disease Model Mice)
1. Administration of Treated Bacterial Product to Chronic Renal Disease Model Mice The test was conducted according to the schedule shown in FIG. 3. Male C57BL/6 mice (CLEA Japan, Inc.) were fed with normal diet (CE-2, CLEA Japan, Inc.) until 6-week old. At the age of 7-week old, the mice were divided into a normal diet group (Normal) to be fed with normal diet and an adenine diet group (Adenine diet) to be fed with normal diet containing 0.2% adenine (made by Wako). Six weeks later, to the Normal group, gavage administration of 0.2 mL/mouse of PBS(−) was performed using a gastric tube once daily for 12 days.

The adenine diet group, which was fed with adenine diet for 6 weeks and then returned to the normal diet, was divided into a PBS(−) administration group (RF) and treated bacterial (*B. longum* CLA8013) product administration groups (RF+8013E(1), RF+8013E(10)). To the RF group, the RF+8013E(1) group, and the RF+8013E(10) group, gavage administration of 0.2 mL/mouse of PBS(−), 8013E(1), and 8013E(10), respectively, was performed using a gastric tube once daily for 12 days.

18 hours after the final administration, dissection was performed.
2. Measurement of Blood Urea Nitrogen (BUN)

Figure 4:
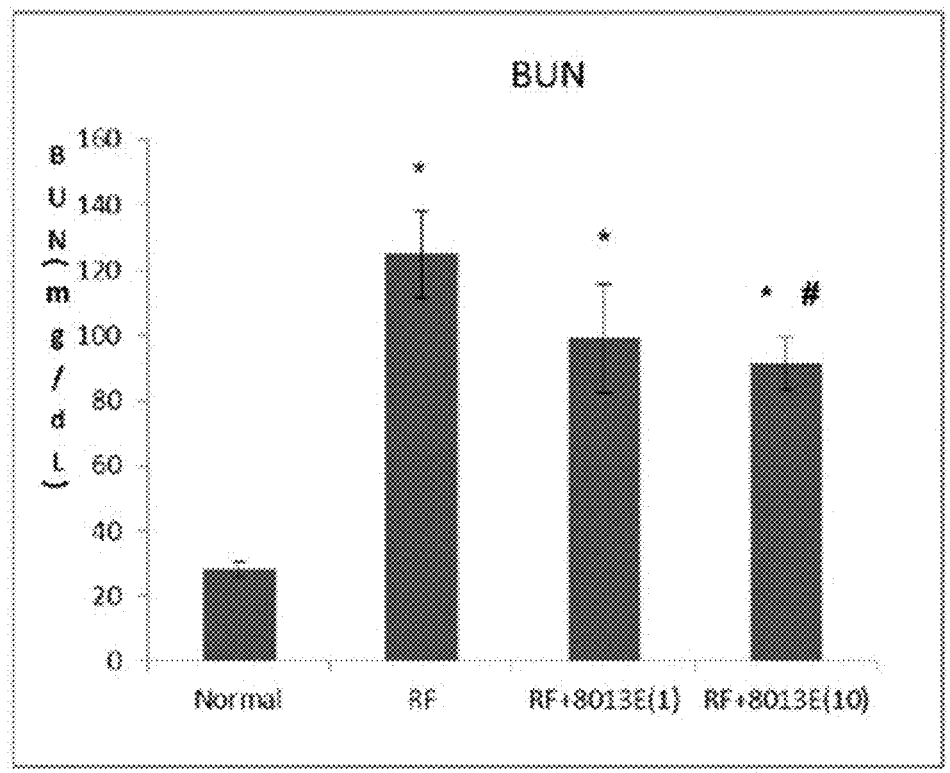
FIG. 4 is a graph showing the measurement results of BUN values.

The results of BUN in mice in each group measured using DetectX Urea Nitrogen Colorimetric Detection Kit (made by ARBOR ASSAYS) are shown in FIG. 4. For each group, 5 or 6 mice were subjected to the measurement. The obtained results are shown as the mean±SD (*: $p<0.05$ vs Normal, #: $p<0.05$ vs RF, Steel-Dwass test). As compared with the Normal group, elevation of the BUN level as an index of renal function was observed in the RF group. In the RF+8013E(1) group and the RF+8013E(10) group, the BUN level was lowered as compared with the RF group. A dose-dependent effect of 8013E was observed, and there was a significant difference between the RF+8013E(10) group and the RF group. The results show that 8013E improved the renal function. During the test period, the body weight was decreased due to the adenine diet, and recovered after the diet was returned to the normal at the start time of test drug administration. The administration of 8013E did not affect the weight recovery, and the same trend as in the RF group was shown.

Example 3 (Preparation of Treated Bacterial Product)

Preparation Method of Treated Product of Bacteria (*Bifidobacterium longum* CLA8013)

Cryopreserved cells of *B. longum* CLA8013 (about $1\times10^8$ cells) were anaerobically cultured using 10 mL of GAM medium (Nissui Pharmaceutical) containing 1% glucose and 0.1% Polysorbate 80 at 37° C. for 30 hours. Subsequently, the culture was centrifuged (3,000×G, 10 min, R.T.) and the supernatant was discarded. The cells were washed with PBS (−), resuspended in 10 mL of PBS (−), and left to stand under anaerobic conditions at 37° C. for 24 hours. After centrifugation, the supernatant was filtered through a filter (0.22 µm) to prepare the filtrate as a treated product (8013E) of bacteria (*B. longum* CLA8013).

Figure 5:
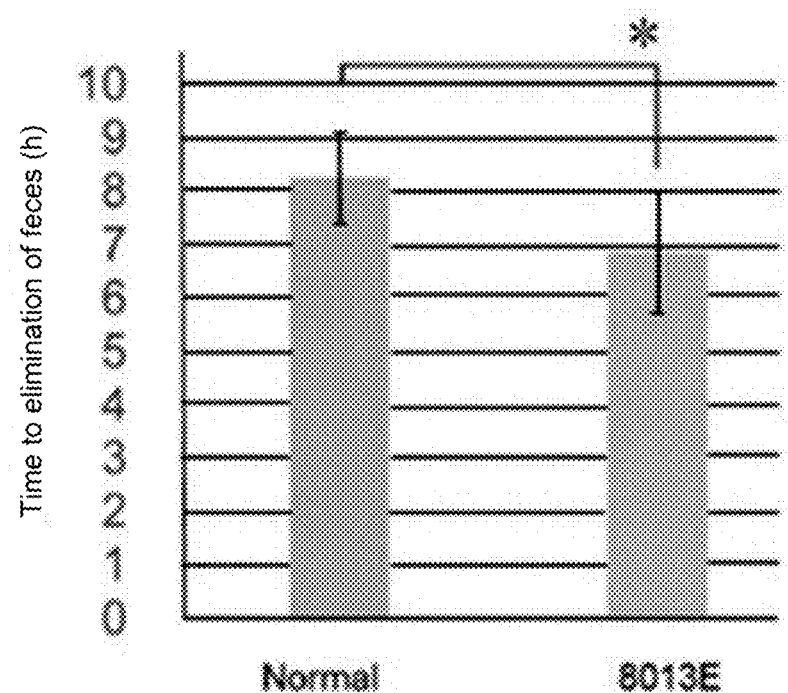
FIG. 5 is a graph showing the measurement results of time to elimination of red-colored feces.

(Ability of Treated Bacterial Product for Transport Throughout the Intestine)
1. Administration of Treated Product of Bacteria (*Bifidobacterium longum* CLA8013) to SD Rats Male SD rats (Japan SLC) at the age of 6 weeks were separately prebred for a week. After the preliminary breeding, the rats were divided into a Normal group and an 8013E group. To the Normal group and the 8013E group, gavage administration of 0.5 mL/rat of PBS(−) and 8013E, respectively, was performed one time. After that, gavage administration of 1 mL/rat of a carmine (Wako) solution (3 g/50 mL, 0.5% carboxymethylcellulose) was performed, one time.
2. Measurement of Ability for Transport Throughout the Intestine in Rats (FIG. 5)

After the administration of the carmine solution, time to red-colored fecal elimination was measured for 8 rats in each group
(*: $p<0.05$ vs control (Mann-Whitney's U test)). The obtained results are shown as the mean±SD. The 8013E group showed significantly shorter red fecal elimination time, which means that 8013E had a defecation promoting effect.

Example 4 (Influence of Solvent Type on Ability for Transcellular Ion Transport)

(Preparation of Treated Bacterial Product)
Preparation Method of Treated Product of Bacteria (*Bifidobacterium longum* CLA8013)

Cryopreserved cells of *B. longum* CLA8013 were anaerobically cultured using 10 mL of GAM medium (Nissui Pharmaceutical) containing 1% glucose and 0.1% Polysorbate 80 at 37° C. for 30 hours. Subsequently, the culture was centrifuged (3,000×G, 10 min, R.T.) and the supernatant was discarded. The cells were washed with PBS (−), resuspended in 10 mL of each solvent (purified water, physiological saline, DMEM/F-12, or PBS (−)), and left to stand under anaerobic conditions at 37° C. for 24 hours. After centrifugation, the supernatant was filtered through a filter (0.22 µm) to prepare the filtrate as a treated product (8013E) of bacteria (*B. longum* CLA8013).
(Cell Culture)

A human colon epithelial cell line T84 was cultured in DMEM/F-12 containing 10% FBS and penicillin/streptomycin. The cells were seeded at $4\times10^4$ cells/cm$^2$, and passaged every 5 to 7 days. The cells were seeded at $5\times10^3$ cells/well on a Snapwell (Costar, 1.13 cm$^2$), and the medium was replaced every 3 days. After cultured for 5 to 7 days, the cells were used in the tests.
(Short-Circuit Current Technique)

The ΔIsc was determined in the same manner as described in the short-circuit current technique in Example 1.
(Ability of Treated Product of Bacteria (*B. longum* CLA8013) for Transcellular Ion Transport)

Figure 6:
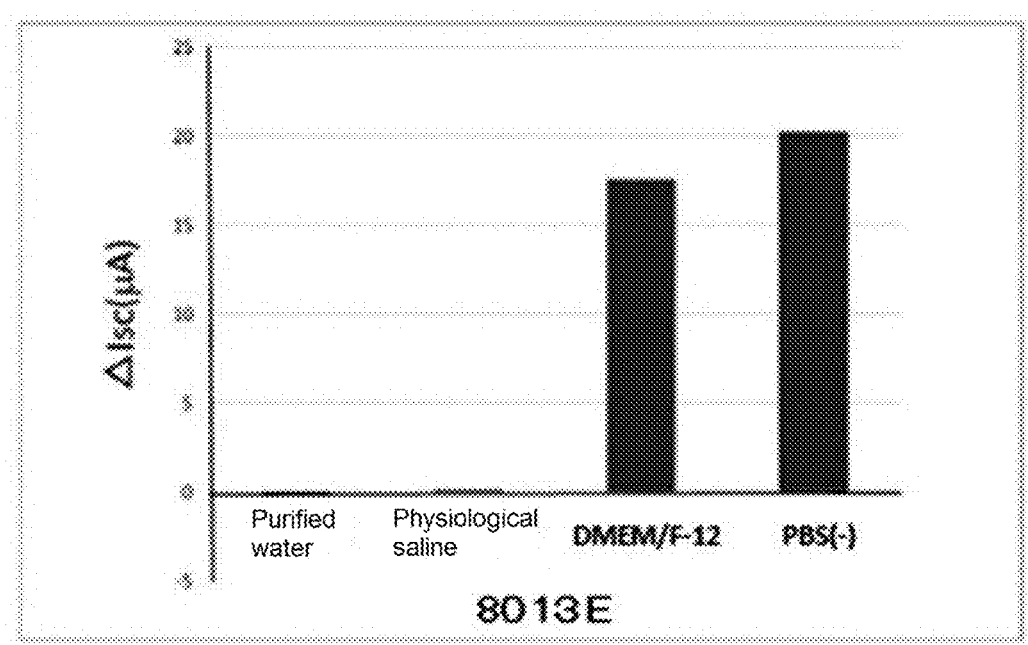
FIG. 6 is a graph showing short-circuit current changes in T84 intestinal epithelium cells in the presence of treated products 8013E treated with different solvents (purified water, physiological saline, DMEM/F-12, and PBS(−)).

The results are shown in FIG. 6. The treated bacterial product prepared using PBS (−) as the solvent had the highest ability for transcellular ion transport, and in the case where the solvent was DMEM/F-12, the ability of the treated bacterial product for transcellular ion transport was the second highest. The results show that by suspending bacterial cells in PBS(−), a treated bacterial product having a higher effect can be prepared. The suspension of bacterial cells in DMEM/F-12 showed no change in pH while left to stand. The results revealed that the increase in the ability of the treated bacterial product for transcellular ion transport is irrelevant to fermentation by the bacteria.

It was also confirmed that in the case where bacterial cells were suspended in sugar-free DMEM/F-12, the treated bacterial product had a high ability for transcellular ion transport.

Example 5 (Preparation of Bacteria)

Preparation Method of Bacteria (*B. longum* MM-2: ID1001)

In the same manner as in Example 2, bacteria (*B. longum* MM-2) were anaerobically cultured for 12 to 18 hours. After that, bacterial cells were recovered and prepared so as to be $5 \times 10^9$ cells/mL in PBS(-) for later use.

(Improving Ability of Bacterial Cells (*B. longum* MM-2) in Chronic Renal Disease Model Mice)

Figure 7:
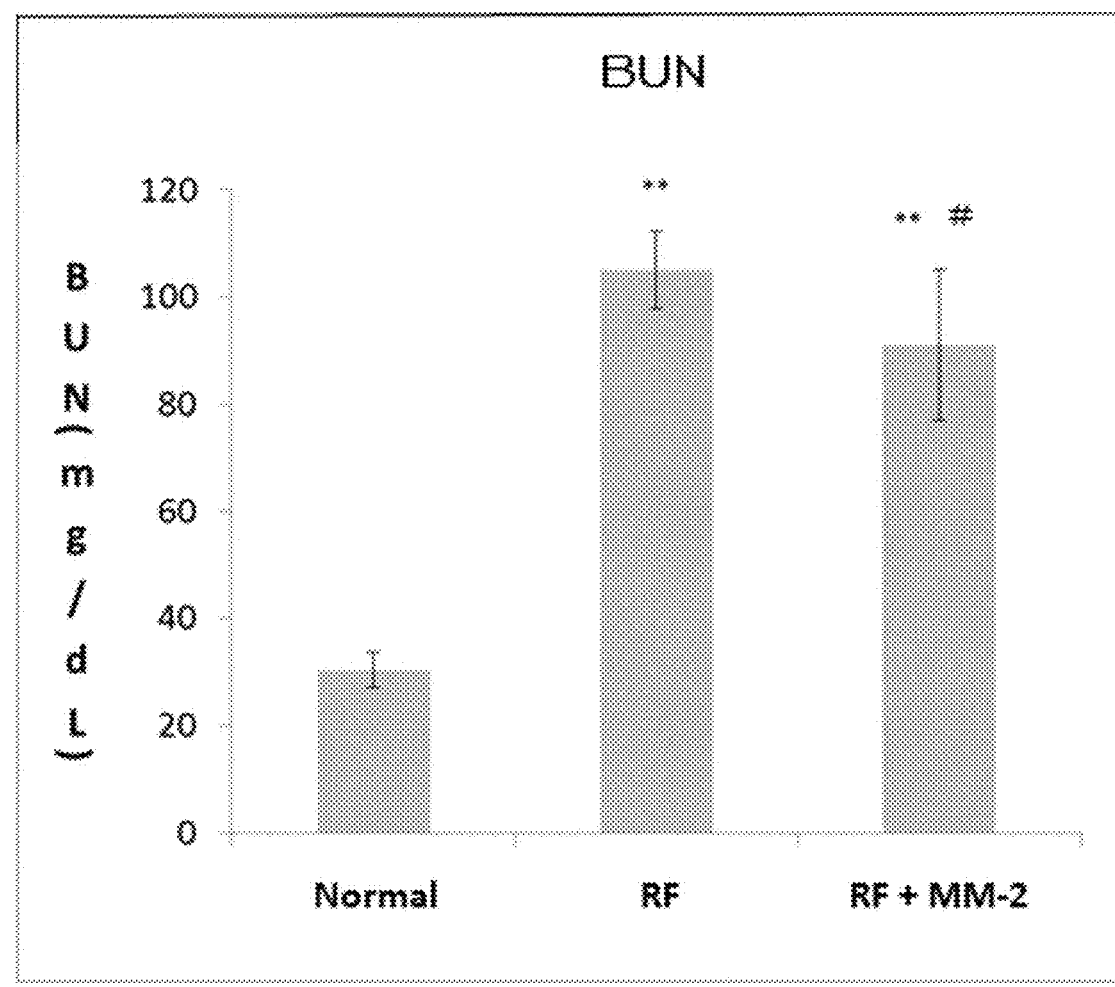
FIG. 7 is a graph showing the measurement results of BUN values.

According to similar schedule and method to those in Example 2, the prepared bacterial cells were administered in a dose of $1 \times 10^9$ cells/0.2 mL/mouse. 18 hours after the final administration, dissection was performed. After that, in a similar manner to that described in Example 2, BUN was measured using 5 or 10 mice for each group. The measurement results are shown in FIG. 7. The obtained results are shown as the mean±SD (**: $p<0.01$ vs Normal, #: $p<0.05$ vs RF). As compared with the Normal group, elevation of the BUN level as an index of renal function was observed in the RF group. In the RF+MM-2 group, the BUN level was decreased as compared with the RF group. The results show that MM-2 bacterial cells improved the renal function. During the test period, the body weight was decreased due to the adenine diet, and recovered after the diet was returned to the normal at the start time of test drug administration. The administration of MM-2 bacterial cells did not affect the weight recovery, and the same trend as in the RF group was shown.

In the present invention, for example, when the bacteria or a treated product thereof to be administered has an equivalent ability for transcellular ion transport to that the MM-2 bacterial strain, administration of the bacteria or a treated product thereof can improve the renal function.

In the present invention, for example, when bacteria without bacterial fermentation are used, administration of a treated product containing the bacteria can also improve the renal function.

Shown below are specific formulations of a pharmaceutical product, a food or drink product, and a feed containing an agent acting on a transcellular ion transporter in the intestinal tract, an agent for activating a chloride channel, an agent for preventing or treating a renal disease, and/or an agent for promoting defecation. The numerical values at the right end in each formulation example mean mass % of each component.

Formulation Example 1: Drug (Tablet)

| | |
|---|---|
| Corn starch | 21.7% |
| Candy powder | 27.1% |
| Dextrin | 29.4% |
| Precipitated calcium carbonate | 13.4% |
| Talc | 3.0% |
| Saccharose | 2.2% |
| Magnesium stearate | 0.5% |
| Treated bacterial product (*Bifidobacterium longum* CLA8013) | 2.7% |

Formulation Example 3: Food or Drink Product (Health Drink)

| | |
|---|---|
| Sugar | 13.3% |
| Citric acid | 0.1% |
| Vitamins | 1.0% |
| Flavor | 0.2% |
| Treated bacterial product (*Bifidobacterium longum* CLA8013) | 14.8% |
| Water | 70.6% |

Formulation Example 6: Feed (Feed for Livestock)

| | |
|---|---|
| Mixed feed | 97.5% |
| Treated bacterial product (*Bifidobacterium longum* CLA8013) | 2.5% |

INDUSTRIAL APPLICABILITY

The agent of the present invention is useful in activation of chloride channels, prevention or treatment of renal diseases, and/or promotion of defecation, and therefore, usable as a medicament, a supplement, etc.

The invention claimed is:

1. A method for activation of a transcellular ion transporter in the intestinal tract, the method comprising administering an agent comprising bacteria of the genus *Bifidobacterium*, or a treated product thereof to a subject in need, wherein the bacteria of the genus *Bifidobacterium* is *Bifidobacterium longum* CLA8013 (Accession Number: NITE BP-02352 and, wherein the treated product is selected from the group consisting of (i) a liquid mixture of the bacterial cells and solvent, (ii) a supernatant or centrifugation supernatant thereof, and (iii) a filtrate obtained by filtering the liquid mixture and the supernatant using a filter.

2. The method according to claim 1, wherein the transcellular ion transporter is a chloride channel.

3. The method according to claim 1, wherein the method further comprises promoting defecation of the subject in need.

4. A composition comprising an effective amount of *Bifidobacterium longum* CLA8013 (Accession Number: NITE BP-02352), wherein said composition is a tablet, a pill, a chewable tablet, a troche, an emulsion, a syrup, an elixir, a soft drink, a lactic drink, fermented milk, yogurt, or a *lactobacillus* drink.

5. A method for activation of a transcellular ion transporter in the intestinal tract, the method comprising administering an agent comprising bacteria of the genus *Bifidobacterium*, or a treated product thereof to a subject in need, wherein the bacteria of the genus *Bifidobacterium* is *Bifidobacterium longum* CLA8013 (Accession Number: NITE BP-02352), wherein the treated product is selected from the group consisting of (i) a liquid mixture of the bacterial cells and solvent, (ii) a supernatant or centrifugation supernatant thereof, and (iii) a filtrate obtained by filtering the liquid mixture and the supernatant using a filter, and wherein the transcellular ion transporter is a chloride channel and wherein the method further comprises promoting defecation of the subject in need.

6. The method according to claim 5, wherein the agent comprises about $1\times10^3$ to $1\times10^{11}$ cells of the bacteria.

7. The method according to claim 5, wherein the agent comprises about $1\times10^6$ to $1\times10^{11}$ cells of the bacteria.

8. The method according to claim 5, wherein the agent comprises about $1\times10^9$ to $1\times10^{11}$ cells of the bacteria.

9. The method according to claim 5, wherein the agent comprises about $1\times10^3$ to $1\times10^{14}$ cells of the treated product.

10. The method according to claim 5, wherein the agent comprises about $1\times10^6$ to $1\times10^{14}$ cells of the treated product.

11. The method according to claim 5, wherein the agent comprises about $1\times10^9$ to $1\times10^{14}$ cells of the treated product.

* * * * *